US006829959B2

(12) United States Patent
Gifford et al.

(10) Patent No.: US 6,829,959 B2
(45) Date of Patent: Dec. 14, 2004

(54) APPARATUS AND METHOD FOR MOVING A SENSOR OVER A WORKPIECE

(75) Inventors: Carl B. Gifford, Buckley, WA (US); Jeffrey R. Kollgaard, Kent, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/291,959

(22) Filed: Nov. 11, 2002

(65) Prior Publication Data

US 2004/0089082 A1 May 13, 2004

(51) Int. Cl.[7] .............................................. G01D 21/00
(52) U.S. Cl. ........................ 73/866.5; 73/588; 73/583; 73/589; 73/613; 73/615; 73/616; 73/633; 73/640; 73/577
(58) Field of Search ................................ 73/866.5, 588, 73/583, 589, 613, 615, 616, 633, 640, 577

(56) References Cited

U.S. PATENT DOCUMENTS

| | | | | |
|---|---|---|---|---|
| 3,628,375 A | * | 12/1971 | Pagano | 73/639 |
| 4,316,390 A | * | 2/1982 | Kretz | 73/620 |
| 4,774,842 A | * | 10/1988 | Kollar et al. | 73/640 |
| 5,567,881 A | * | 10/1996 | Myers | 73/629 |
| 5,698,787 A | | 12/1997 | Parzuchovski et al. | |
| 6,220,099 B1 | | 4/2001 | Marti et al. | |
| 6,339,331 B1 | | 1/2002 | Ruzzo | |

FOREIGN PATENT DOCUMENTS

FR        2772121 A1     6/1999

OTHER PUBLICATIONS

Yoseph Bar–Cohen, Paul Backes; *Open–architecture robotic crawlers for NDE of aircraft structures; Materials Evaluation*; 1999; 11 pages; vol. 57, No. 3; ASNT.

Norm Schehl, Wally Hoppe, Al Berens, Ray Ko; *Evaluation of an Intergranular Corrosion Detection Method on the Structural Repair of Aging Aircraft Program*; The Boeing Corporation and the United States Air Force.

Engineering at Boeing—Automated Inspection Systems; 4 pages; available at <http://www.engineeringatboeing.com/content/mfgquality/quality/automatedsystems.jsp> (visited Sep. 23, 2002).

* cited by examiner

*Primary Examiner*—Hezron Williams
*Assistant Examiner*—André K. Jackson
(74) *Attorney, Agent, or Firm*—Alston & Bird LLP

(57) ABSTRACT

The apparatus and method for moving a sensor over a workpiece includes a sensor, and an actuating member. The sensor, such as a non-destructive test sensor, is carried by the actuating member, and the actuating member is at least partially disposed within a housing. The actuating member is adapted for automated movement in one direction, and the housing may be configured to be grasped by an operator and manually moved in another direction. As such, the sensor may automatically move in one direction with respect to the workpiece without manual intervention, and manually move in another direction, such that the sensor is moved by the combination of automated and manual movement. In addition, the actuating member may have at least two substantially parallel arms extending from near the sensor, which permits the sensor to slide along the workpiece while maintaining a substantially normal relationship to a surface of the workpiece.

27 Claims, 2 Drawing Sheets

APPARATUS AND METHOD FOR MOVING A SENSOR OVER A WORKPIECE

BACKGROUND OF THE INVENTION

This invention relates to techniques for the non-destructive testing of structures, and, in particular, to economical and time-conserving techniques for moving one or more non-destructive sensors relative to the portion of the structure to be tested.

Non-destructive testing of structures involves thoroughly examining a structure without harming the structure or requiring significant disassembly of the structure. Non-destructive testing is advantageous for many applications in which a thorough inspection of the exterior and/or interior of a structure is required. For example, non-destructive testing is commonly utilized in the aircraft industry to inspect aircraft structures for any type of internal or external damage to the structure. Metallic aircraft structures are typically inspected for corrosion and/or cracking, particularly near fasteners in the structure. Composite structures are typically inspected for any type of damage occurring anywhere on or within the composite material.

Various types of sensors may be utilized to perform non-destructive testing. One or more sensors may move over the portion of the structure to be examined, and receive data regarding the structure. For example, a pulse-echo, thru-transmission, or shear wave sensor may be utilized to obtain ultrasonic data, such as thickness gauging, detection of laminar defects and porosity, and/or crack detection in the structure. Resonance, pitch/catch or mechanical impedance sensors may be utilized to provide indications of voids or porosity, such as in adhesive bondlines of the structure. In addition, single and dual current eddy current sensors impart and detect eddy currents within a structure so as to identify cracks and/or corrosion, particularly in metallic or other conductive structures. The data acquired by the sensors is typically processed by a processing element, and the processed data may be presented to a user via a display.

In many cases, structures must be inspected in the field because it is either not feasible or too expensive and time-consuming to transport the structure to an off-site laboratory for the inspection. For routine field inspections of structures, technicians typically manually scan the structures with an appropriate sensor. The manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor approximately one-fourth of an inch in another direction. For a technician standing beside a structure, the technician may repeatedly move the sensor right and left, and back again, while indexing the sensor about one-fourth of an inch between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician and interpreting the displayed data. Thus, manual scanning of structures, is time-consuming, labor-intensive, and prone to human error. Furthermore, manual scanning may cause fatigue and/or other health problems for technicians, such as Repetitive Motion Disorders.

Automated inspection systems have been developed, but the automated systems may sometimes be too expensive and/or bulky to be utilized for routine field inspections. For example, the Mobile Automated Scanner (M.A.U.S.), developed by The Boeing Company, provides automated data acquisition in a portable package for on-site inspections. One type of M.A.U.S. system automatically moves along the structure via strategically controlled suction cups, while another type includes handheld sensors and an associated carriage that is moved along the structure via manual motion. As such, the M.A.U.S. system not only scans the structure, but also processes the data regarding the structure, and associates the data with the exact location on the structure from where the data was obtained. While the M.A.U.S. system is portable, provides fast inspection rates, and employs any type of sensor, such as those mentioned above, it may also be large and somewhat expensive due to the processing element(s) required to provide the detailed data regarding the scanned portion of the structure. In addition, the M.A.U.S. system is not capable of being powered by a local power supply, such as batteries, and therefore requires a connection to a remote power supply via bulky power cable(s), which hinders the ease of use of the system. Additionally, the version of the M.A.U.S. system that includes handheld sensors is similarly limited by the relatively large size of the handheld sensors and the associated cabling. As such, it may not be feasible to utilize the M.A.U.S. system for routine field inspections.

Therefore, a need exists for a portable scanning technique that reduces the tasks technicians must perform as compared to a manual scanning technique. The need is also for a technique that is lower cost and easier to use than conventional automated scanning techniques.

BRIEF SUMMARY OF THE INVENTION

The apparatus and method for moving a sensor in at least one direction according to the present invention provides a technique for scanning a workpiece with a scanner that is more compact and lower in cost than the conventional automated scanning techniques. Furthermore, the scanning technique provided by the present invention is partially automated, such that the amount of physical labor performed by a scanning technician is greatly reduced. Thus, the present invention provides a low cost and time-saving scanning technique that may be efficiently utilized for many applications, even routine field inspections of various structures.

The apparatus for providing a combination of automated and manual movement of a non-destructive test (NDT) sensor according to the present invention includes an NDT sensor, a housing and an actuating member. The NDT sensor is carried by the actuating member, and the actuating member is at least partially disposed within the housing. The actuating member is adapted for automated movement in one direction, while the housing is configured to be grasped by an operator and manually moved in another direction. The sensor may be secured to the actuating member with at least one adjustment member. One example of a sensor that may be used is an eddy current sensor.

According to the method for providing a combination of automated and manual movement of an NDT sensor, once the sensor is positioned proximate a workpiece, the sensor may be automatically moved in one direction with respect to the workpiece without manual intervention, and manually moved in another direction, such that the sensor is moved by the combination of automated and manual movement. For instance the manual motion may be in a direction at least substantially normal to the automatic movement.

The actuating member may have at least two substantially parallel arms extending from near the sensor, which permits the sensor to contact the surface while maintaining the sensor in a substantially normal relationship to the surface of the workpiece. In one embodiment of an apparatus for moving a sensor over a workpiece, the apparatus includes a sensor and the actuating member having the parallel arms described above. Thus, the sensor attached to the actuating member may be positioned proximate the workpiece, and the sensor may then slide along the surface such that the sensor continuously contacts the surface and is maintained in a substantially normal relationship to the surface of the workpiece while it slides.

The apparatus also may include a cam having an eccentric collar. As the cam rotates, the eccentric collar may slide within an elongated opening defined by the actuating member, which, in turn, causes the sensor to move in the one direction. The elongated opening is located a distance from the sensor, and a motor may be used to cause the cam to rotate.

Embodiments of the present invention may also involve attaching a pivot piece to the actuating member a predetermined distance from the sensor. The actuating member is then capable of at least partially pivoting about the pivot piece to cause the sensor to move in the one direction. In further embodiments of the present invention, the actuating member may be balanced, such as by attaching a weight to the actuating member opposite the sensor relative to the pivot piece. In embodiments of the present invention in which the actuating member has at least two substantially parallel arms, the arms may extend from the sensor to the pivot piece.

Thus, the apparatus and method for moving a sensor in at least one direction along a surface provides a low cost, and efficient technique for scanning the surface of a structure with a non-destructive sensor. In particular, the scanning technique of the present invention is less expensive, more compact, and easier to use than conventional automated scanning techniques, while also less time-consuming, more exact, and takes less of a physical toll on a scanning technician than conventional manual scanning techniques.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The apparatus and method for moving a sensor relative to a workpiece according to the present invention provide a technique for scanning a surface of a structure with a scanner that is more compact and lower in cost than the conventional automated scanning techniques. Furthermore, the scanning technique provided by the present invention is partially automated, such that the amount of physical labor that must be performed by a scanning technician is greatly reduced and such that the accuracy of the results is generally improved relative to the manual techniques. Thus, the present invention provides a low cost and time-saving scanning technique that may be efficiently utilized for many applications, even routine field inspections of various structures.

Figure 1:
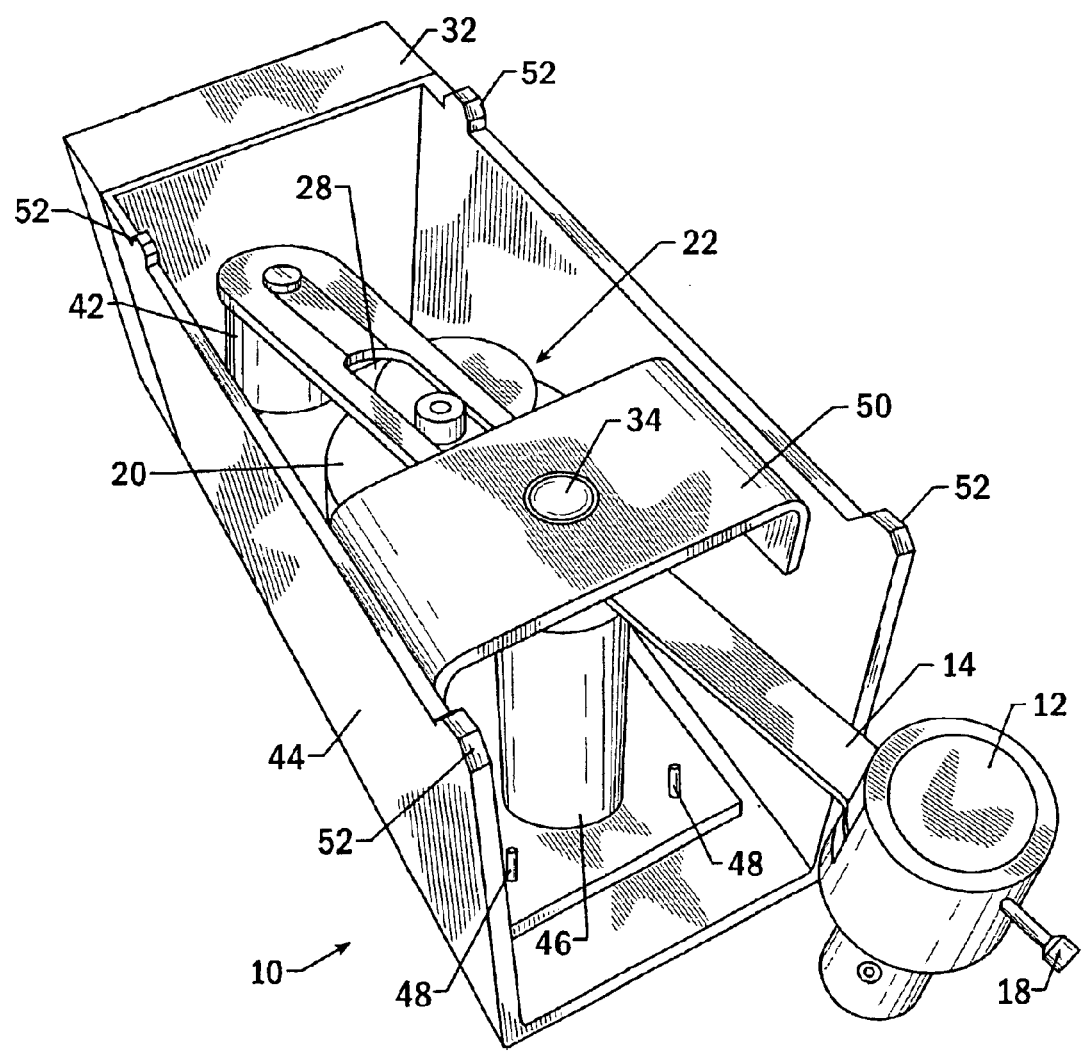
FIG. 1 is a perspective view of an apparatus for moving a sensor relative to a workpiece according to one embodiment of the present invention.
Figure 2:
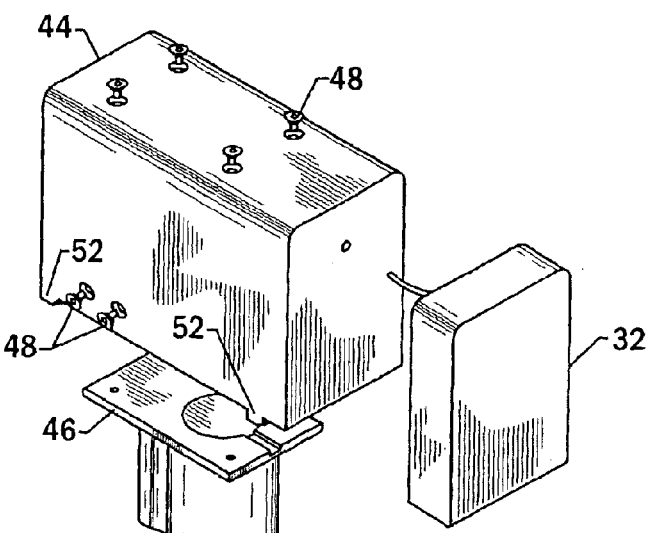
FIG. 2 is an exploded view of an apparatus for moving a sensor relative to a workpiece according to one embodiment of the present invention.

One embodiment of the apparatus for moving a sensor relative to a workpiece according to the present invention is shown in FIG. 1. The apparatus 10 includes a sensor 12 and an actuating member 14. FIG. 1 is a view of the bottom of the embodiment of the apparatus 10, wherein the bottom of the apparatus 10 is defined as the portion of the apparatus that faces the structure to be inspected. As such, the sensor 12 is positioned proximate the bottom of the apparatus 10 to face the structure to be inspected. FIG. 2 further illustrates an exploded view of the embodiment of the apparatus 10 depicted in FIG. 1.

The sensor 12 may be any type of sensor known to those skilled in the art and utilized to inspect structures. The sensor 12 is typically a non-destructive sensor, such that the sensor is capable of inspecting a structure without harming the structure or requiring disassembly of the structure. In the embodiment of the apparatus 10 shown in FIG. 1, the sensor 12 is an eddy current sensor. Single and dual eddy current sensors are capable of detecting cracks and/or corrosion, particularly in metallic or other conductive structures. Other examples of sensors 12 are pulse-echo, thru-transmission, shear wave, resonance, pitch/catch, and mechanical impedance sensors. Pulse-echo, thru-transmission and shear wave sensors provide ultrasonic data, such as for thickness gauging, detection of laminar defects and porosity, and/or crack detection in the structure. Resonance, pitch/catch or mechanical impedance sensors provide indications of voids or porosity, such as in adhesive bondlines of the structure.

The sensor 12 is typically in communication with a processing element to process the data accumulated by the sensor, and optionally, a display to visually present the processed data. In many cases, communications cable(s) transmit data between the sensor 12 and the processing element and/or display. In other embodiments, the data may be transmitted between the sensor 12 and the processing element and/or display via wireless communications. The sensor 12 may be directly connected to the processing element and/or display, or indirectly connected, such as via a network. In further embodiments of the present invention the processing element and/or display may be located proximate to the sensor 12, such that remote connections between the sensor, processing element and/or display are not necessary.

The actuating member 14 carries the sensor 12. In one embodiment, the actuating member 14 defines an aperture 16 to receive the sensor 12. The aperture 16 is shown in the embodiments of the actuating member 14 illustrated in FIGS. 1, 2 and 3. The aperture 16 in the illustrated embodiments is shown near an end portion of the actuating member 14. In other embodiments, however, the aperture for receiving the sensor 12 may be defined in any other portion of the actuating member 14 or the actuating member may carry the sensor in other manners. The aperture 16 may be any shape, so long as the aperture is as large or larger than the largest diameter sensor that is capable of being utilized in the apparatus 10. The actuating member 14 is preferably made of a relatively resilient and non-conductive material that is also relatively flexible. For example embodiments of the actuating member 14 may be made of a nylon material, such as Delrin™, commercially available from E.I. Du Pont De Nemours and Company Corporation.

To secure a sensor 12 within the aperture 16, at least one adjustment element 18 may be adjusted appropriately. As shown in FIG. 1, the adjustment element 18 may be a threaded member, such as a screw, which secures the sensor within the aperture by entering the aperture through a correspondingly threaded opening that extends through the actuating member to the aperture 16. As such, the desired sensor 12 may be positioned within the aperture 16, then the screw may be adjusted until the sensor 12 is secured between the actuating member 14 and the screw. In other embodiments, the one or more adjustment element(s) may be positioned and/or shaped such that the adjustment element(s) secure the sensor within the aperture without the sensor 12 contacting the actuating member 14.

The actuating member 14 may be activated in any manner known to those skilled in the art to cause the actuating member to move in such a way that the sensor 12 moves in one direction relative to the surface to be inspected. For instance, the actuating member, and thus, the sensor may move back and forth in one direction, such that the sensor 12 moves over at least a portion of the desired inspection area of a structure. As used herein, the direction in which the actuating member moves the sensor refers to the direction defined by the reciprocating motion of the sensor and may be linear, a circular, semi-circular, or any other type of motion. Although not necessarily, the actuating member 14 may move along one or more rails or the like to define the desired type of movement of the actuating member 14 and sensor 12.

The apparatus 10 may employ any type of mechanical, electrical and/or electromechanical means for creating and controlling the movement of the actuating member 14 and the sensor 12. For instance, in the embodiments of the apparatus 10 illustrated in FIGS. 1 and 2, the actuating member 14 may be set into motion by a motor 20, and the movement of the actuating member 14 may be controlled by a cam system 22. The motor 20 may be any type of motor known to those skilled in the art. In one embodiment of the apparatus 10 of the present invention, the motor 20 is a gear motor, such as a gear motor commercially available from Micro Mo Electronics, Inc., which causes a shaft attached to the motor to rotate. The speed of rotation depends upon the gear ratio of the motor. The torque of the motor 20 should be sufficient to move the sensor 12 via the actuating member 14 over the desired surface. For instance, in embodiments in which the sensor 12 contacts the surface, the torque of the motor should be chosen to ensure that the sensor 12 is capable of moving over the surface, even if the surface is uneven and/or rough, and even if the surface includes protruding fasteners. In embodiments in which the sensor 12 does not directly contact the surface or encounter any type of impediment to its motion, the torque of the motor may be lower, if desired.

Power for the motor 20 may be provided in any manner known to those skilled in the art. Preferably, power is supplied to the motor 20 via a local power supply 32, such as batteries. Although, in alternative embodiments of the apparatus 10 of the present invention, the motor 20 may be powered by a remote, stationary or portable power supply, a local power supply 32 is preferred in order to eliminate the need for a power cable between the remote power supply and the motor 20. Thus, the lack of power cables and other types of cables between the apparatus 10 and other equipment is an advantage of the present invention as compared to existing automated scanning systems for scanning a surface with a sensor, which are bulky and require multiple cables between the scanning system and remote equipment. In contrast, the embodiment of the apparatus that includes a local power supply is much more independent and portable.

Figure 4:
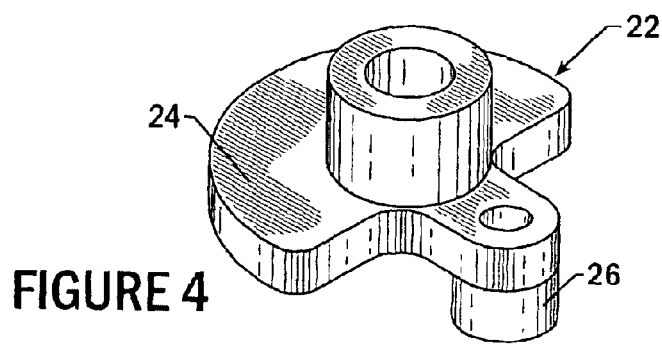
FIG. 4 is a perspective view of a cam and eccentric collar for an apparatus for moving a sensor relative to a workpiece according to one embodiment of the present invention.

In the embodiment of the apparatus 10 illustrated in FIGS. 1 and 2, the motor 20 drives a cam system. One embodiment of the cam system 22 is shown in FIG. 4, which includes a cam 24 and an eccentric collar 26. The cam 24 is operably attached to the motor and rotates as it is driven by the motor. For instance, the cam 24 may be a partially semi-circular disk with an attachment piece on one side, as shown in FIG. 4. The semi-circular shape of the cam 24 is advantageous in some embodiments of the apparatus, particularly in embodiments in which the cam 24 rotates relatively fast, to balance the weight of the cam about the point where the cam 24 attaches to the motor 20, which prevents vibration of the actuating member 14 and the sensor 12. In other embodiments of the present invention, the cam 24 may be any other suitable shape, such as circular, square, or the like. The cam 24 may be made of any type of metallic or non-metallic material that is sufficiently resilient to withstand the repetitive motion and pressures to which the cam is subjected during operation. In one embodiment of the present invention, the cam 24 is made of aluminum. The motor 20 is secured to the cam 24 via the attachment piece in any appropriate manner. For instance, the attachment piece may fit securely about or within the shaft of the motor that rotates with a fastener adapted to fasten the attachment piece to the shaft of the motor. Alternatively, the attachment piece may be secured to the shaft of the motor with an attaching compound, such as an adhesive, epoxy, cement or the like. Regardless of the manner of attachment, the attachment piece is aligned with the axis of rotation of the shaft driven by the motor.

The collar 26 may be formed as part of the cam 24, or it may be a separate piece that may be attached to the cam 24. In the embodiment of the cam system 22 shown in FIG. 2, the collar 26 is a separate piece that may be attached to the cam 24 in any appropriate manner. For instance, the cam 24 may include an opening to receive and secure a portion of the collar 26, or to receive a fastener to fasten the collar 26 to the cam 24. In other embodiments, the collar 26 may be secured to the cam 24 with an attaching compound, such as an adhesive, epoxy, cement or the like. Regardless of the manner in which the collar 26 is attached to the cam 24, the collar 26 is eccentric with respect to the cam. Thus, the collar 26 is not aligned with the axis of rotation of the shaft of the motor, and therefore, not aligned with the attachment piece of the cam 24. In addition, the collar 26 may be located on the side of the cam 24 that is opposite the attachment piece. The collar 26 may also be made of any type of appropriately resilient metallic or non-metallic material. In addition, because the collar 26 slides within the actuating element 14, as described hereinbelow, the collar 26 may be made of a non-marring material. For example, the collar 26 may be made of Delrin™ material, commercially available from E.I. Du Pont De Nemours and Company Corporation.

The collar 26 cooperates with the actuating member 14 to move the actuating member in the desired manner. As such, the actuating member 14 may define an elongated opening 28, which is located a distance from the sensor. The distance between the elongated opening 28 and the sensor depends upon the range of motion of the actuating member 14 that is desired. For instance, if a broad range of motion of the actuating member 14 is desired, then the elongated opening 28 is further away from the sensor than if a smaller range of motion is desired. The size of the elongated opening 28 is large enough to receive the collar 26, and to permit it to move within the elongated portion of the opening as the cam 24 rotates. For example, in one embodiment of the actuation member 14, the elongated opening is approximately seven-eighths of an inch long.

In operation, the cam 24 may be attached to the motor 20, and the collar 26 may be eccentrically attached to the cam 24. The actuating member 14 may then be positioned appropriately, such that the collar 26 is within the elongated opening 28. Prior or subsequent to positioning the actuating member 14, at least one sensor 12 may be secured within the aperture(s) 16, such that the sensor(s) 12 face the surface when the apparatus 10 is positioned on the surface. The sensor(s) 12 may contact the surface or be positioned a predetermined distance from the surface, depending upon the requirements of the sensor(s) 12. When the motor 20 is activated, the cam 24, and therefore, the collar 26 rotate. As the collar 26 rotates, it moves along the elongated opening 28 of the actuating member 14, which, in turn, causes the actuating member 14 and, in turn, the sensor(s) 12, to move in one direction. As a result of the design of the cam assembly, the collar eventually reverses its direction of movement within the elongated opening such that the actuating member and, in turn, the sensor, similarly reverse direction. As such, the sensor is moved in one direction in a reciprocating fashion.

Figure 3:
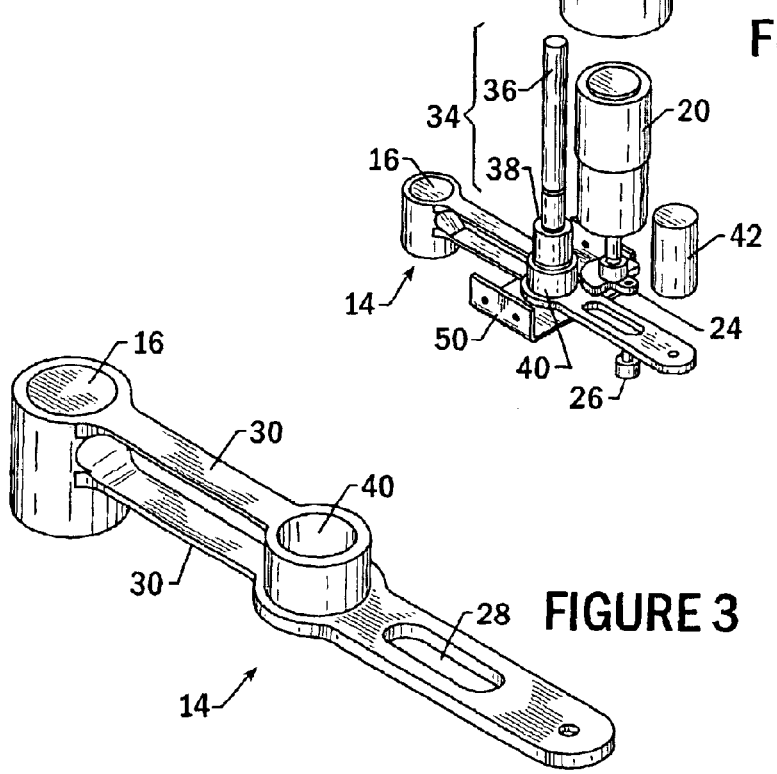
FIG. 3 is a perspective view of an actuating member of an apparatus for moving a sensor relative to a workpiece according to one embodiment of the present invention.

In embodiments of the apparatus 10 in which the sensor(s) 12 contact the surface, the sensor(s) should be capable of moving over even a relatively rough and/or contoured surface while maintaining continuous contact with and the desired orientation to the surface, such as a perpendicular orientation. In one embodiment of the apparatus 10 of the present invention, the actuating member 14 may include at least two substantially parallel arms 30 extending from a portion of the actuating member 14 proximate to the aperture 16, as shown in FIG. 3. For example, the arms may extend from the aperture 16 to the pivot piece 34, and be less than 50 percent of the length of the actuating member 14. In a specific embodiment of the actuating member 14, the parallel arms 30 are approximately one and a half inches long. The arms 30 are also preferably made of a relatively resilient and non-conductive material that is also relatively flexible. For example embodiments of the actuating member 14 and/or the arms 30 may be made of nylon, plastic, and/or a Delrin™ material, commercially available from E.I. Du Pont De Nemours and Company Corporation.

To further control the movement of the actuating member 14, a pivot piece 34 may be attached to the actuating member 14, which is shown in FIG. 2. The pivot piece 34 is stationary, such that the actuating member 14 at least partially pivots about the pivot piece 34. The pivot piece 34 may be attached to the actuating member 14 at any point to provide the desired type of control over the movement of the actuating member. For instance, as shown in the embodiment of the FIG. 2, the pivot piece is attached to the actuating member at a distance from the aperture 16, which receives the sensor 12. Thus, the distance between the pivot piece 34 and the sensor 12 may depend upon the desired range of movement of the sensor 12. For example, the shorter the distance between the pivot piece 34 and the sensor 12, the smaller the range of movement of the sensor 12, and the longer the distance between the pivot piece 34 and the sensor 12, the larger the range of movement of the sensor 12.

The pivot piece 34 may be attached to the actuating member 14 in any manner known to those skilled in the art. For example, in the embodiment of the apparatus 10 of the present invention shown in FIG. 2, the pivot piece 34 may include a pivot rod 36 and a roller bearing 38. The pivot rod 36 and roller bearing 38 are shaped such that the roller bearing 38 is capable of at least partially rotating on a portion of the pivot rod 36, while simultaneously being attached to the pivot rod 36. The pivot rod 36 is preferably made of a high-strength metallic and/or non-metallic material. For instance, in a preferred embodiment of the present invention, the pivot rod 36 is made of steel.

In one embodiment of the apparatus 10 of the present invention, the pivot rod 36 has at least partial circumferential grooves that are capable of receiving retaining rings, such as the retaining rings commercially available from W. M. Berg, Inc., part number Q1–25. A roller bearing 38 may therefore be rotationally held onto pivot rod 36 by the retaining rings that prevent the roller bearing 38 from moving axially along the pivot rod 36. For example, the roller bearing 38 of this embodiment may be a roller bearing such as that commercially available from W. M. Berg, Inc., part number NRB-47. In other embodiments, the roller bearing 38 may be rotationally held onto pivot rod 36 in any other manner known to those skilled in the art, such as with any other cooperating means between the roller bearing 38 and the pivot rod 36.

In addition, the actuating member 14 is capable of receiving the roller bearing 38. As shown in the embodiment of the actuating member 14 of FIG. 3, the actuating member 14 may include a receptacle 40 to receive the roller bearing 38. The roller bearing 38 may be attached within the receptacle 40 in any manner known to those skilled in the art, such as with friction, an adhesive compound, a fastener, or the like. The pivot rod 36 therefore may be capable of extending through the roller bearing 38 and the receptacle 40 to the opposite side of the actuating member 14 from the receptacle 40, where the pivot rod 36 may be secured. In other embodiments of the apparatus 10 of the present invention, the pivot rod 36 may not extend completely through the receptacle 40 and/or the actuating member 14. Regardless of the degree of extension of the pivot rod 36 through the receptacle and/or the actuating member 14, the actuating member 14, in conjunction with the roller bearing 38, is capable of at least partially rotating about the pivot rod 36.

Depending upon the weight of the sensor 12 secured to the actuating member 14, the actuating member 14 may be balanced in order to ensure that the actuating member, and thus the sensor 12, moves evenly over the surface. For instance, in embodiments of the apparatus 10 of the present invention that include a pivot piece 34 about which the actuating member 14 pivots, the weight of the sensor 12 located on one side of the pivot piece 34 may cause the actuating member 14 to wobble or experience some other type of undesirable movement when the actuating member 14 is in motion. To prevent the undesirable movement of the actuating member 14 described above, a weight 42 may be applied on the side of the actuating member 14 that is opposite the sensor 12 relative to the pivot point, as shown in the embodiment of FIG. 2. Although the weight 42 is shown having a cylindrical shape in FIG. 2, it may be any appropriate shape that provides the amount and balance of weight that is required to counter-balance the sensor 12 with respect to the actuating member 14. In addition, the weight 42 may be attached to the actuating member 14 in any manner known to those skilled in the art, such as with any type of fastener. In embodiments in which the sensor(s) 12 may be removed and replaced with other sensors of varying sizes and weights, the weight 42 may similarly be removed and replaced to provide the appropriate counter weight. In alternative embodiments of the apparatus 10 of the present invention, the undesirable movement of the actuating member 14 due to the weight of the sensor 12, may be prevented in any other manner known to those skilled in the art. For instance, if the actuating member 14 does not need to be flexible in order to allow the sensor to continuously contact the surface as it moves relative to the surface, then the actuating member 14 may be reinforced with or made of a relatively high-strength material that prevents the undesirable movement of the actuating member due to the weight of the sensor.

As shown in FIGS. 1 and 2, the components of the apparatus 10 may be at least partially contained within a housing 44. To retain the various components of the apparatus 10 within the housing, a support 46 may be attached within the housing 44. The support 46 may be attached to housing 44 in any appropriate manner, such as with fasteners 48, adhesive compound, or the like. In other embodiments of the housing 44, the support 46 may be formed as part of the housing 44. The support 46 may retain the components of the apparatus 10 in any manner such that the components are positioned relative to one another in the necessary working relationship, and such that the components are capable of being positioned as desired relative to a surface. For example, FIGS. 1 and 2 illustrate the support 46 retaining the motor 20 and the pivot rod 36. Thus, the support 46 is shaped to receive the motor 20 and the pivot rod 36. The motor 20 and the pivot rod 36 may be retained in the support 46 in any manner known to those skilled in the art, such as with friction, fasteners, adhesive compound or the like. The cam system 22 is also retained within the housing 44 because it is attached to the motor 20, as described hereinabove.

The actuating member 14 is also at least partially retained within the housing 44, such as with bracket 50. The bracket 50 may also be attached to the housing 44 in any appropriate manner, such as with fasteners 48, adhesive compound, or the like. In other embodiments of the housing 44, the bracket 50 may be formed as part of the housing 44. The bracket 50 retains the actuating member 14 in any manner known to those skilled in the art. For instance, as shown in FIGS. 1 and 2, the pivot rod 36, which extends through the roller bearing 38 and the receptacle 40 is retained by the bracket 50, which, in turn, retains the actuating member 14. As shown, a portion of the actuating member 14 including that portion that carries the sensor may extend beyond the housing. Since the portion of the hosing facing the surface to be tested is generally open, the actuating member and the sensor may be disposed within the housing, if desired. The housing 44 is sized to be grasped by the operator, for example the housing is typically 1.9 inches wide, 2.95 inches high, and 4 inches long. In addition, the housing is sized such that it does not restrict the reciprocal motion of the sensor.

The housing 44 may be positioned on the surface to be inspected by the sensor 12, such that the sensing portion of the sensor 12 faces the surface in the desired positioned relationship, such as in contact with the surface or a spaced relation to the surface. The actuating member 14 may then be activated, such as by activating the motor 20 that controls the movement of the actuating member 14, and thus the movement of the sensor 12. The sensor 12 then moves in one direction over the surface. The housing 44 may then be manually moved along the surface in a desired direction. To facilitate movement of the housing 44 along the surface, the housing 44 is preferably made of a non-conductive and non-marring material, such as nylon, plastic, and/or a Delrin™ material, commercially available from E.I. Du Pont De Nemours and Company Corporation. Thus, the housing 44 will not harm the surface as it moves along the surface. The housing 44 also may have feet 52 located along the edges of the housing 44. The feet 52 are also preferably made of a non-conductive and non-marring material, such as nylon, plastic, and/or a Delrin™ material, in order to protect the surface as the feet 52 slide along the surface. The feet 52 also facilitate movement of the housing 44 along the surface because the feet 52 may be easier to maneuver over the surface than the edges of the housing 44, and because the feet 52 provide a passage for articles protruding from the surface, such as fasteners.

Thus, the apparatus 10 and method for moving a sensor in at least one direction provide a faster, more exact, and easier technique for scanning a surface with a sensor than the manual method. As such, the scanning technicians are not subjected to the physical fatigue that accompanies the manual method, and the object with the surface to be scanned is not retained out of service for the relatively long time that is required to perform manual scanning. In addition, the apparatus 10 and method for moving a sensor in at least one direction according to the present invention is less expensive, less bulky and easier to use than the conventional automated scanning techniques. Because the apparatus 10 does not require significant processing equipment or cables to remote equipment, it is easier to maneuver and easier to utilize in a field environment, in addition to being much less expensive, than complicated automated scanning systems.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for providing a combination of automated and manual movement of a non-destructive test (NDT) sensor, comprising:

an NDT sensor;

a housing; and an actuating member at least partially disposed within said housing, said actuating member carrying said sensor, and adapted for automated movement in one direction relative to said housing, wherein said actuating member comprises at least two substantially parallel arms at least partially disposed in said housing and extending proximate to said sensor to maintain said sensor in a substantially normal relationship to a workpiece under test;

wherein said housing is configured to be grasped by an operator and manually moved in another direction such that said sensor is moved by the combination of automated and manual movement.

2. An apparatus for providing a combination of automated and manual movement of a non-destructive test (NDT) sensor, comprising:

an NDT sensor;

a housing;

an actuating member at least partially disposed within said housing, said actuating member carrying said sensor, and adapted for automated movement in one direction, wherein said actuating member defines an elongated opening located a distance from said sensor; and a cam having an eccentric collar that slides within the elongated opening defined by said actuating member as said cam rotates to cause said sensor to experience movement in the one direction, wherein said housing is configured to be grasped by an operator and manually moved in another direction such that said sensor is moved by the combination of automated and manual movement.

3. The apparatus according to claim 2, further comprising a motor for causing said cain to rotate.

4. The apparatus according to claim 1, further comprising a pivot piece, wherein said pivot piece is attached to said actuating member such that said actuating member at least partially pivots about said pivot piece to cause said sensor to experience movement in the one direction.

5. The apparatus according to claim 4, wherein said pivot piece is attached to said actuating member a predetermined distance from said sensor.

6. An apparatus for providing a combination of automated and manual movement of a non-destructive test (NDT) sensor, comprising:

an NDT sensor;

a housing;

an actuating member at least partially disposed within said housing, said actuating member carrying said sensor, and adapted for automated movement in one direction;

a pivot piece, wherein said pivot piece is attached to said actuating member such that said actuating member at least partially pivots about said pivot piece to cause said sensor to expenence movement in the one direction; and a weight attached to said actuating member opposite said sensor relative to said pivot piece to balance said actuating member, wherein said housing is configured to be grasped by an operator and manually moved in another direction such that said sensor is moved by the combination of automated and manual movement.

7. The apparatus according to claim 1, wherein said actuating member comprises at least one adjustment element to secure said sensor to said actuating member.

8. The apparatus according to claim 1, wherein said sensor is an eddy current sensor.

9. A method for providing a combination of automated and manual movement of a non-destructive test (NDT) sensor, comprising:

positioning the sensor housing and a sensor proximate a workpiece under test, wherein the sensor is carried by an actuating member;

automatically moving the sensor in one direction with respect to the workpiece and relative to the sensor housing without manual intervention regarding motion in the one direction, wherein automatically moving the sensor comprises rotating a cam that engages the actuating member in order to move the actuating member and the sensor carried thereby in the one direction; and manually moving the sensor housing in another direction such that the sensor is moved by the combination of automated and manual movement.

10. The method according to claim 9, wherein automatically moving the sensor comprises automatically moving the sensor in a reciprocating motion with respect to the workpiece.

11. The method according to claim 9, wherein manually moving the sensor housing is concurrent with automatically moving the sensor.

12. The method according to claim 9, wherein automatically moving the sensor comprises sliding the sensor along the workpiece.

13. The method according to claim 12, wherein sliding the sensor comprises continuously contacting the workpiece with the sensor while maintaining the sensor in a substantially normal relationship to a surface of the workpiece.

14. An apparatus for moving a sensor over a workpiece, comprising:

a sensor; and an actuating member for carrying said sensor, wherein said actuating member causes said sensor to experience movement over the workpiece, and wherein said actuating member comprises at least two substantially parallel arms that carry said sensor, said at least two substantially parallel arms extending proximate to said sensor and positioned such that one arm is closer to the workpiece than another arm to permit said sensor to contact the workpiece while maintaining said sensor in a substantially normal relationship to a surface of the workpiece.

15. An apparatus for moving a sensor over a workpiece, comprising:

a sensor;

an actuating member for carrying said sensor, wherein said actuating member causes said sensor to experience movement over the workpiece, wherein said actuating member comprises at least two substantially parallel arms proximate said sensor to permit said sensor to contact the workpiece while maintaining said sensor in a substantially normal relationship to a surface of the workpiece, and wherein said actuating member defines an elongated opening located a distance from said sensor; and a cam having an eccentric collar that slides within the elongated opening defined by said actuating member as said cam rotates to cause said sensor to move over the workpiece.

16. The apparatus according to claim 15, further comprising a motor for causing said cam to rotate.

17. The apparatus according to claim 14, further comprising a pivot piece, wherein said pivot piece is attached to said actuating member such that said actuating member at least partially pivots about said pivot piece to cause said sensor to move over the workpiece.

18. The apparatus according to claim 17, wherein said pivot piece is attached to said actuating member a predetermined distance from said sensor.

19. An apparatus for moving a sensor over a workpiece, comprising:

a sensor;

an actuating member for carrying said sensor, wherein said actuating member causes said sensor to expenence movement over the workpiece, and wherein said actuating member comprises at least two substantially parallel arms proximate said sensor to permit said sensor to contact the workpiece while maintaining said sensor in a substantially normal relationship to a surface of the workpiece;

a pivot piece, wherein said pivot piece is attached to said actuating member such that said actuating member at least partially pivots about said pivot piece to cause said sensor to move over the workpiece; and a weight attached to said actuating member opposite said sensor relative to said pivot piece to balance said actuating member.

20. The apparatus according to claim 17, wherein the arms of said actuating member extend from said sensor to said pivot piece.

21. The apparatus according to claim 14, further comprising a housing at least partially surrounding at least one of said actuating member and said sensor.

22. The apparatus according to claim 14, wherein said actuating member comprises at least one adjustment element to secure said sensor to said actuating member.

23. The apparatus according to claim 14, wherein said sensor is an eddy current sensor.

24. An apparatus according to claim 1 wherein said actuating member defines an aperture in which said sensor is disposed, and wherein said at least two substantially parallel arms extend to that portion of said actuating member that defines the aperture.

25. An apparatus according to claim 1 wherein one of said substantially parallel arms is positioned closer to the workpiece than another one of said arms.

26. An apparatus according to claim 24 wherein said actuating member defines an aperture in which said sensor is disposed, and wherein said at least two substantially parallel arms extend to that portion of said actuating member that defines the aperture.

27. An apparatus according to claim 14 further comprising a housing, wherein said at least two substantially parallel arms are at least partially disposed in said housing.

* * * * *

UNITED STATES PATENT AND TRADEMARK OFFICE
CERTIFICATE OF CORRECTION

PATENT NO. : 6,829,959 B2 Page 1 of 1
DATED : December 14, 2004
INVENTOR(S) : Gifford et al.

It is certified that error appears in the above-identified patent and that said Letters Patent is hereby corrected as shown below:

Column 11,
Line 26, "cain" should read -- cam --.

Signed and Sealed this

Eighth Day of March, 2005

JON W. DUDAS
*Director of the United States Patent and Trademark Office*